(12) United States Patent
Gobel et al.

(10) Patent No.: US 8,147,449 B2
(45) Date of Patent: Apr. 3, 2012

(54) DEVICE FOR GASTRIC FEEDING AND DRAINAGE VIA AN ARTIFICIAL STOMA

(75) Inventors: Fred Gobel, Wilhelmsfeld (DE); Donald Jay McMichael, Roswell, GA (US); Lanita Grayce Cox, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 603 days.

(21) Appl. No.: 11/922,296

(22) PCT Filed: Jun. 14, 2006

(86) PCT No.: PCT/EP2006/005733
§ 371 (c)(1),
(2), (4) Date: Dec. 14, 2007

(87) PCT Pub. No.: WO2006/133927
PCT Pub. Date: Dec. 21, 2006

(65) Prior Publication Data
US 2009/0312701 A1  Dec. 17, 2009

(30) Foreign Application Priority Data
Jun. 17, 2005  (DE) .......................... 10 2005 028 428

(51) Int. Cl.
*A61M 29/00* (2006.01)

(52) U.S. Cl. ............ 604/96.01; 604/164.01; 604/103.07
(58) Field of Classification Search ............... 604/96.01, 604/910, 912, 170.01–170.03, 164.01, 103.07
See application file for complete search history.

(56) References Cited

U.S. PATENT DOCUMENTS

| 4,850,953 | A | | 7/1989 | Haber et al. |
|---|---|---|---|---|
| 5,545,179 | A | * | 8/1996 | Williamson, IV ............ 606/213 |
| 5,720,734 | A | * | 2/1998 | Copenhaver et al. ......... 604/247 |
| 7,691,079 | B2 | * | 4/2010 | Gobel ........................ 604/96.01 |

FOREIGN PATENT DOCUMENTS

| WO | WO 94/15655 A2 | | 7/1994 |
|---|---|---|---|
| WO | WO 96/36283 A1 | | 11/1996 |
| WO | WO 00/47117 A1 | | 8/2000 |
| WO | WO 2004/069057 | * | 8/2004 |
| WO | WO 2004/069057 A2 | | 8/2004 |
| WO | WO 2005/009292 A1 | | 2/2005 |

* cited by examiner

*Primary Examiner* — Theodore Stigell
(74) *Attorney, Agent, or Firm* — Karl V. Sidor; Sue C. Watson

(57) ABSTRACT

The invention describes a closure device for the provision of freshly created gastric feeding fistulas, the basis of the design of the device being an introverted balloon that allows a sealing and hemostatic axial traction movement on the fistula that is to be sealed, the concentric balloon ends which run transmurally through the stomach and abdominal wall being arranged in a special seal-promoting and hemostatic manner.

7 Claims, 10 Drawing Sheets

DEVICE FOR GASTRIC FEEDING AND DRAINAGE VIA AN ARTIFICIAL STOMA

PRIORITY

This patent application claims priority to currently copending German National Application DE 10 2005 028 428.0 entitled "Vorrichtung zur gastrischen Ernährung und Drainage über eine transkutan angelegte Fistel" filed on Jun. 17, 2005 by Microcuff, GmbH having Dr. Fred Göbel named as inventor.

BACKGROUND OF THE INVENTION

The present invention relates to a device for creating and maintaining an artificial stoma enabling access to a body cavity, such as used in the direct feeding of a patient's stomach. More particularly, the present invention relates to a device for percutaneously placing various gastric catheters, forming artificial stomas capable of accessing the gastrointestinal tract, and ultimately providing a gastric feeding capability. Beyond the initial placement procedure, the device meets the requirements for permanent placement in the patient, such that when used for enteral feeding, the device enables a low-force, dynamically self-adjusting, directed seal between the inside of the stomach or gastric wall and an external body surface, i.e., the outside of the abdominal wall.

In particular, the invention addresses the problem of the seal or permanent fusion of the tissues surrounding the stoma that needs to be established between the abdominal cavity and the inside of the stomach immediately after the surgical creation of the fistula, i.e., during the initial insertion of the catheter. It also is concerned with ways in which subsequent to placement, the catheter can be changed simply and atraumatically, even by a trained layperson, without damaging the stoma site.

It is recognized that numerous medical conditions exist in which it becomes necessary to gain percutaneous access to viscera such as the stomach or small intestines. Situations where a patient has lost the ability to swallow and will require long term nutritional support may dictate feeding directly into the stomach or jejunum. Feeding in this manner may be accomplished by inserting a feeding tube into the patient's stomach such that one end remains anchored in the stomach, while the other end remains external to the patient's body for connection to a nutrient source. A variety of different feeding tubes or catheters intended for enteral feeding have been developed over the years, including some having a "low profile" relative to the patient during use and those having the more traditional or non-low profile configuration.

Such feeding tubes may be inserted into a patient's stomach in a number of ways. Feeding tubes may be endoscopically placed, surgically placed through an open incision, laproscopically placed, or percutaneously placed under endoscopic, fluoroscopic or ultrasonic guidance. Different types of feeding tubes may be placed using these procedures, examples include gastrostomy, jejunostomy or gastro-jejunostomy. These tubes may be retained in the lumen (stomach or intestine) with a variety of retention anchors. These anchoring mechanisms include: inflatable balloons, obturatable domes, fixed dome-type bumpers, or suture wings.

It is known that many of the catheters on the market today are commonly referred to as "replacement" catheters because they are substituted for an enteral feeding tube that is initially placed in a patient for six to eight weeks until a fistula stoma tract is established. Once the stoma tract is established, the initial placement device is generally removed, and the "replacement" enteral feeding device is inserted into the stoma tract. Historically, prior to placing the actual enteral feeding device, it has been preferred to perform a gastropexy procedure during placement. This procedure enables the physician to attach the visceral wall to the abdomen and to create the stoma tract through the two. This attachment is critical to prevent inadvertent separation and exposure of the peritoneal cavity to contamination and possible peritonitis.

Initial placement devices are often not readily removable without additional invasive surgical procedures. That is, many initially placed enteral catheters contain rigid retention members which cannot readily be passed through the stoma of the patient when it is desired to remove the initially placed device. Typically the t-shaped fastener or t-bar is not removable and is left in the body cavity where it is allowed to pass naturally in the patient's stool. In many cases the t-bar is not passed and remains within the body cavity. Moreover, during the six to eight weeks it takes for the fistula's stoma tract to be established, the anchoring mechanism of the prior art gastropexy device which typically consists of a small metal t-shaped fastener may embed itself into the gastric or intestinal wall and ultimately lead to infection. Furthermore, the t-bar itself may have sharp edges which can be uncomfortable for the patient.

In many of these procedures, in order to achieve the desired seal between the stomach and the abdominal wall, a traction force must be applied to the anchoring mechanism. The force is applied in such a way as to pull the stomach cavity to the abdominal wall so that the penetration through both may heal together thereby creating the passage or stoma leading from the patient's stomach, through the abdominal wall, to an external environment. It is necessary to apply this traction force for a period of a couple of days through a couple of weeks until the stoma site adequately heals. During this period the patient has reduced mobility which may lead to additional post-operative complications.

There is a need and desire for a device which may be used during initial placement or creation of a stoma site and which also may serve as the "replacement" enteral feeding device itself Such a device would foster the permanent fusion of the stomach wall to the abdomen; it would replace standard catheter placement technology and thus substitute a single step procedure for the standard multi-step procedure. This would serve to reduce the invasiveness of the procedure, greatly enhance wound healing, and enable immediate, post-placement gastric access for feeding and drainage, and ultimately allow atraumatic exchange of the low profile device.

SUMMARY OF THE INVENTION

In response to the foregoing problems and difficulties encountered by those of skill in the art, the present invention is directed toward a device for the creation of an artificial stoma into and subsequent fluid transfer to or from a living body. Such a device may provide the following advantages: it would foster approximation of the gastric wall and abdominal wall in a sufficiently large area to enable tissue fusion; it would reduce the number of punctures to only one transcutaneous gastric puncture or incision; it would create a self-adjusting seal with respect to the puncture site and do so while taking into account body movement and resulting sheer forces; it would provide secure anchoring even under high pull-forces; it would reduce or prevent initial leakage or bleeding from the puncture channel thus reducing the likelihood of peritoneal infections; it would allow immediate access to the stomach and maintain the initial and continuous dilation of the puncture channel; it would reduce the risk of ulceration within the gastric lumen due to low-pressure filling of the balloon; it would enable enhanced patient mobility and comfort; and it would provide one device, meeting the requirements of both initial and long-term placement.

The above-mentioned problems and difficulties can be solved by a device according to independent claim 1. Further advantageous features, aspects and details of the invention are evident from the dependent claims, the description, and the drawings.

The device in one embodiment would include a thin foil having a first and a second end with a length disposed therebetween. The thin foil would be arranged in a manner such that one of said ends is backfolded or introverted into the other of said ends. A cap having at least one port therethrough would also be provided. The cap would securely capture each end of the foil. The port would terminate between the first and second foil ends within a space created by introversion of the foil. By application of an inflation source to the port, the length of the foil would inflate and form a generally torus shaped balloon having both exterior and interior externally facing concentric surfaces. The cap is situated at one end of the balloon.

In many embodiments, the device would contain a bore through the cap so that communication with a passage formed by the interior externally facing surface may be had. Such communication would pass through the interior of the device. In many embodiments, the torus shaped balloon may be adapted to exert an increasingly greater force upon increasing inflation, the force being exerted axially along the foil and directed toward the cap.

Some embodiments may be provided with an insertion device used for placing the foil in a deflated state within the living body and situating the cap adjacent a body surface at the stoma. The insertion device may contain a user manipulable introducer and a capturing element. The introducer may be configured as a tapered probe having a cavity therein within which the foil is temporarily captured. The capturing element would be sized to fit frictionally within the bore and in conjunction with the foil would retain the introducer in position proximate to the cap. An extension rod may be affixed to the introducer. The extension rod would enable the tapered probe to be inserted deeper into the living body until the foil is disengaged from within the cavity. This could be accomplished without affecting the position of the cap or the capturing element To remove the introducer, the balloon is inflated and the introducer is extracted from the living body by passing it out via the passage and bore, again, subsequent to inflation of the balloon and removal of the capturing element.

The device in any of its embodiments may be adapted to be placed in the living body by engaging a guide wire previously situated in the living body, a process known and understood by those of skill in the art.

According to one specific embodiment, the present invention relates to a device for supplying patients by means of a transcutaneous fistula (stoma) for direct feeding into the stomach, comprising a balloon which is backfolded in itself, whereby the inner end of the balloon serves as an open lumen for inserting a feeding catheter therethrough, whereby moreover an axially oriented tractive force acts between the balloon and the ends of the balloon, which causes a force component pressing the inner abdominal wall onto the stomach, and whereby on the body surface a disc element and/or a diameter of the outer one of the two concentric ends of the balloon, enlarged at least about 25% compared to the ratio of the diameter of the fistula, serves as a bearing for an axially oriented back rolling of a torus onto the inner stomach wall.

Specifically, the diameter of the outer of the two concentric ends of the balloon may be larger than about 50 to about 75% of the fistula.

Other objects, advantages and applications of the present invention will be made clear by the following detailed description of a preferred embodiment of the invention and the accompanying drawings wherein reference numerals refer to like or equivalent structures.

DETAILED DESCRIPTION OF THE PRESENT INVENTION

In response to the foregoing challenges that have been experienced by those of skill in the art, the present invention is directed toward making initial feeding catheter placement less invasive and more comfortable for the patient. The invention is intended to reduce complications associated with enteral feeding and the initial placement of the enteral feeding device such as bleeding or leakage of gastric fluids. It provides a single device capable of accommodating both the procedure of placement and long-term wear and use which addresses the needs associated with initial as well as prolonged placement of the catheter.

To solve these problems, the invention envisions an introverted or backfolded balloon arrangement similar to that described, in a basic form, in WO 2004/069057 to Dr. Lothar Göbel, which is incorporated fully herein by reference. It should be understood that the introversion of one end of a balloon element through the opposite end produces a "torus" shape. In the inflated state, this torus structure has the tendency to move the balloon ends into a median plane of the torus ring. A tractive force operates axially between the balloon and the balloon ends, thus serving, in the present invention, as an important basic functional element.

If the balloon ends are passed through the fistula channel and secured outside the body on the outside wall of the abdomen within a fixing cap element, the resulting axial tractive force would generate a force component capable of pressing the stomach against the inside wall of the abdomen. This would permit the permanent fusion of the two tissue layers which prior to this device would have necessitated a separate treatment step prior to the actual placement of the enteral feeding device and intra-gastric access channel through the fused tissue. This torus shaped closing element would also allow immediate access to the stomach through a free central lumen of the element. This lumen may be used for immediate feeding, drainage or insertion of a catheter therethrough.

An initial version as well as alternative embodiments of such a device has been described in DE 10 2005 028 428.0 entitled "Vorrichtung zur gastrischen Ernährung und Drainage über eine transkutan angelegte Fistel" and was filed on Jun. 17, 2005 by Dr. Fred Göbel. As such, this disclosure is also fully incorporated herein by reference and this application claims priority thereto.

Figure 1:
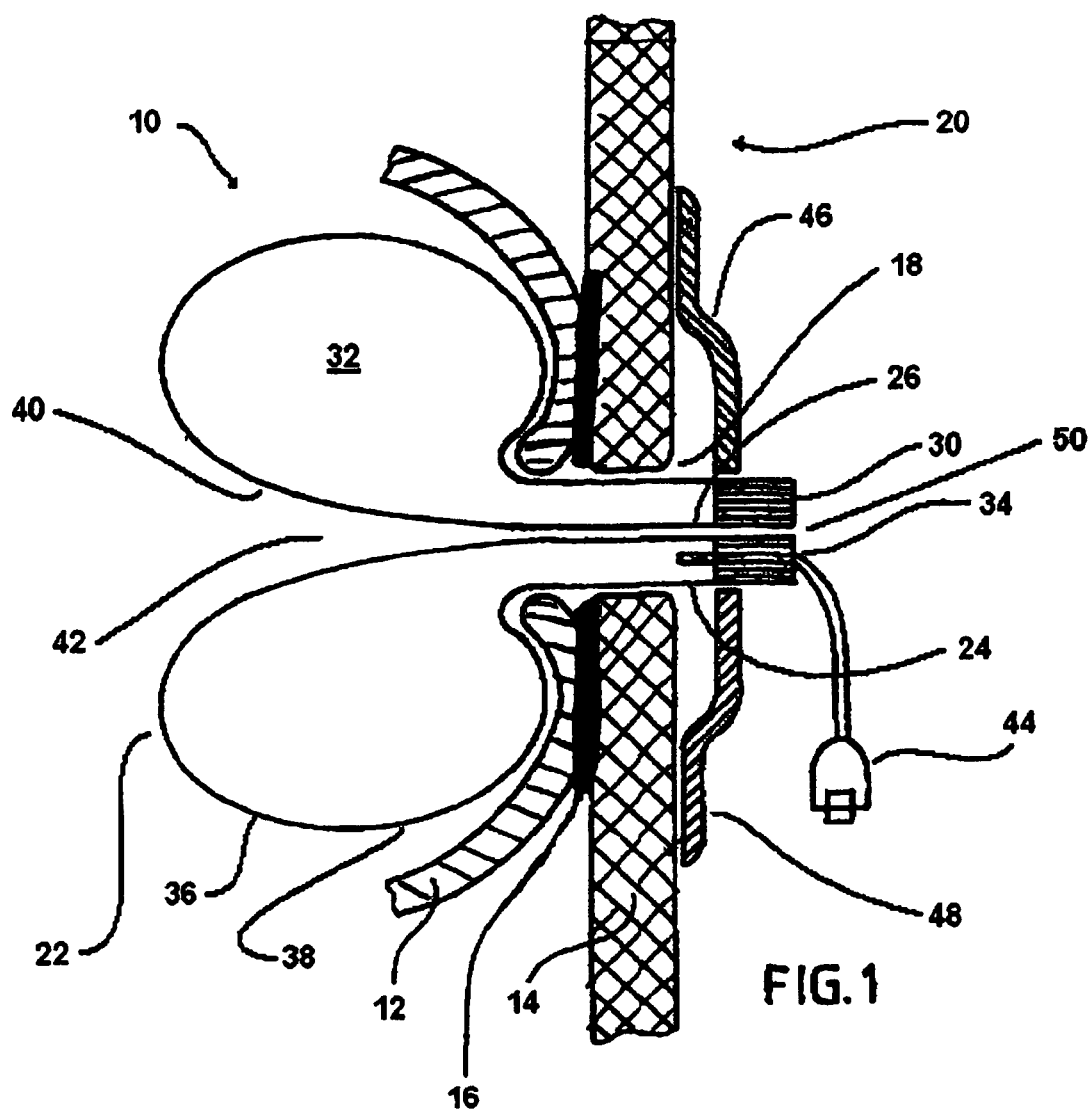
FIG. 1 depicts an illustrative view of one embodiment of the present invention.

Looking now to FIG. 1, a device 10 in accordance with the present invention is depicted. FIG. 1 depicts the spatial relationships between the device 10 and the adjacent organs to it: the gastric wall 12, the abdominal wall 14 and the anatomical fusion site 16 between the two wall structures 12 and 14, where the perforation forming the fistula or stoma 18, in a patient's living body 20, is situated. At this point, it should be understood that for convenience the description of the device will generally be directed toward accessing the stomach, for example, to enterally feed a patient. However, the devices as shown and described herein may also be used to create a communication between two cavity located organs, spaces or structures, or one cavity located organ, space or structure and an external environment. As such, no limitations specifically requiring the invention to be associated with enteral feeding or gastric access should be read into the specification.

Figure 2:
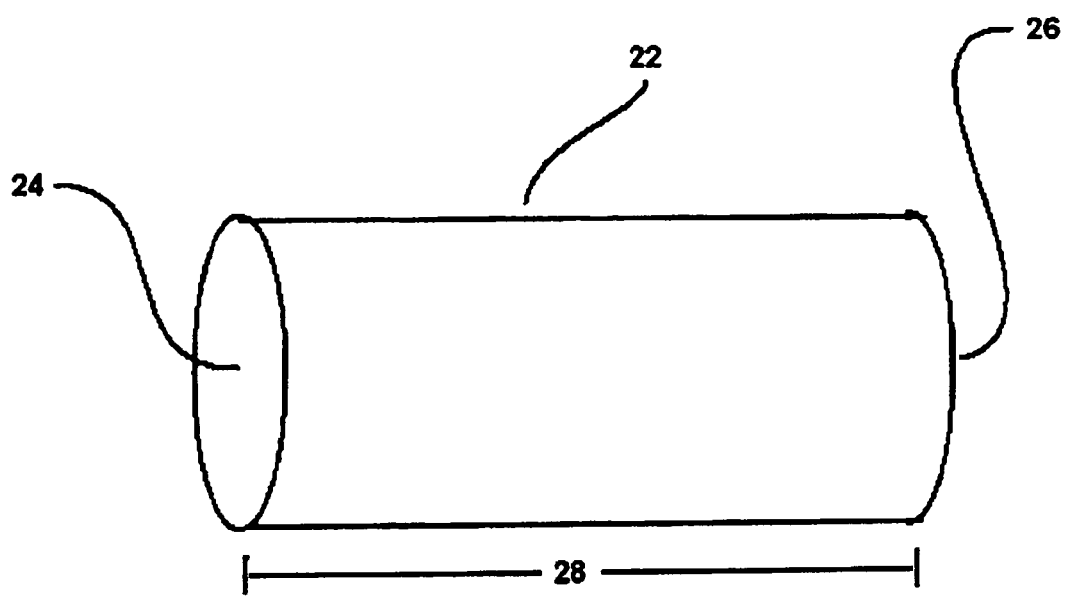
FIGS. 2 and 3 depict intermediate steps in the creation of the backfolding principle described in many of the embodiments of the present invention.

In many of the contemplated embodiments, the device 10 is formed from a thin foil 22 having first and second ends 24 and 26 respectively. As shown in FIG. 2, the foil 22 may be cylindrical in shape and have a length 28 disposed between the ends 24 and 26, which along with the ends may define a three-dimensional volumetric space bounded by a surface or surfaces formed by the foil itself. Among the simplest of volumetric spaces is the cylinder, as shown. However, other contemplated volumetric shapes may include the sphere, cube, cone, cylinder, and more generally, the polyhedra.

Figure 3:
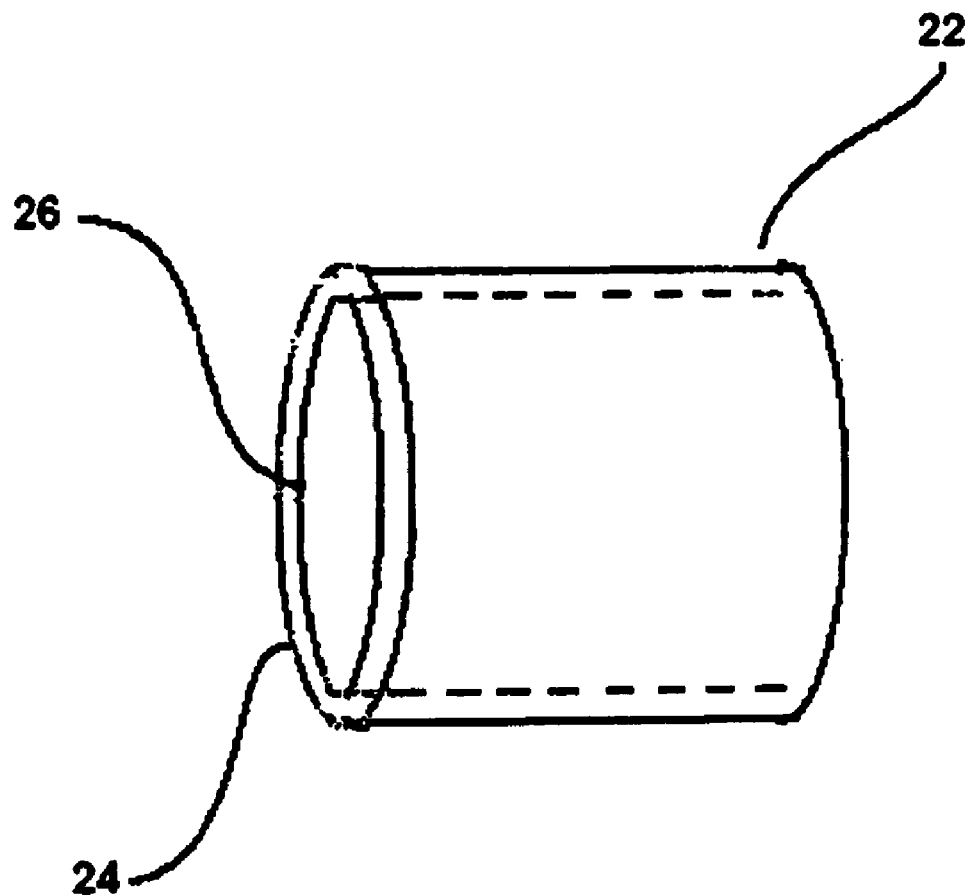

In common embodiments, and referring to the cylindrical embodiment of FIG. 2 in particular, FIG. 3 depicts one of the ends of the foil 22 being backfolded or introverted into the other, for example, end 26 may be backfolded into end 24 such that end 26 is situated within end 24. Of course, this configuration may be switched with end 24 situated within end 26 and still perform in accordance with the invention.

In any event turning back to FIG. 1, it may be seen that by capturing the ends 24 and 26 within a cap 30, an interior space 32 is created. This space 32 is created by the introversion of the foil 22 itself and may be seen to be defined by its length 28 and bounded by its ends 24 and 26. Providing the cap 30 with a port 34 that terminates within this space 32 between the first foil end 24 and the second foil end 26 creates a torus shaped structure or balloon 36 having exterior and interior externally facing surfaces 38 and 40 respectively. The space 32 forms the interior of the balloon 36 and is adapted to inflate and deflate upon application or removal of a fluid source such as air, water, or saline. Other fluids may be used and would be understood by those of skill in the art.

The surface 38 may be seen to be an externally facing, exterior surface of the balloon 36. The surface 40 is also an exterior surface, however, it is considered an internally facing, exterior surface of the balloon in that it forms a passage 42 through the center of the torus shaped balloon yet does not enter the space 32. The diameter of this passage 42 formed by the surface 40 in many embodiments is smaller than the puncture channel through the gastric 12 and abdominal wall 14. The diameter of the passage 42 determines the flow-characteristics through the device. Further, secondary catheter elements, described below, may be inserted into the passage 42 if desired.

In order to inflate the balloon 36, an inflation source or mechanism 44 of some kind should be capable of connection to the port 34. As stated above, the fluid used to inflate the balloon 36 may be a suitable gas or liquid, such as air or saline. A retention mechanism 46 may also be provided in order to hold the device 10 properly within the living body 20. Such a retention mechanism 46 is envisioned to have numerous possible configurations each of which will be discussed at greater length in this specification. In a first embodiment, the retention mechanism 46 may be configured as a simple disc, button, or retaining ring 48. The retaining ring 48 may be secured to the cap 30 or to the balloon 36 itself via a friction fit and may simply be adapted to slidably attach to the exterior of the device in some manner so that it may be slid against the skin of the abdominal wall of the patient when in place.

A bore 50 through the cap 30 connects the passage 42 to an external environment. The bore 50 forms an opening through which fluids may pass into or out of the living body 20. In many embodiments, the bore 50 enables the injection of enteral feeding solutions. It may also be used to vent gases or other fluids from within the cavity as described in more detail below. However, in any of the embodiments described, dedicated pathways may be provided, one for feeding and one for venting. This concept would be readily understood by those of skill in the art and may be accommodated by numerous configurations including but not limited to the insertion of a dedicated catheter 52 through the bore 50, through the passage 42, and into the stomach or other organ within which the device is in communication. Such a catheter may be seen in FIGS. 5 through 7 which will be further described below. The catheter 52 may have dual lumens, one for feeding and one for venting. Alternatively, the catheter 52 may be used for one of the functions whereas the other function is performed by ensuring that there is ample room between the exterior of the catheter and the passage 42 and/or bore 50 diameters.

Referring generally back to this principle of an introverted foil 22 forming a torus shaped balloon 36, it may be seen that this is an improvement over the prior art devices currently in existence. For example, it should be noted that the present device 10 forms a shaftless catheter structure which effectively eliminates the need for the prior art rigid shaft elements. It should also be understood by those of skill in the art that unlike a balloon bearing a rigid shaft, the present invention may be reduced to a collapsed tape-like structure when in the deflated and evacuated state. With such a device 10, it would be possible to insert the balloon portion 36 through the stoma 18 and into the living body 20 via a low-invasive, small bore access penetration.

Furthermore, due to the controllable collapsibility of the device 10 it is more amenable to atraumatic removal from the stoma than are prior art devices. This is because the present invention does not require the significant trans-abdominal exertion typically associated with those prior art devices containing a rigid shaft element for carrying the balloon component. In the prior art devices, the mechanics of the balloon member are typically altered negatively over time, for example, balloon members associated with the prior art are known to stiffen and lose their ability to retract fully into the shaft completely. This results in the creation of traumatizing folds that may exacerbate healing of the stoma site upon removal or subsequent manipulation of the catheter.

Figure 4:
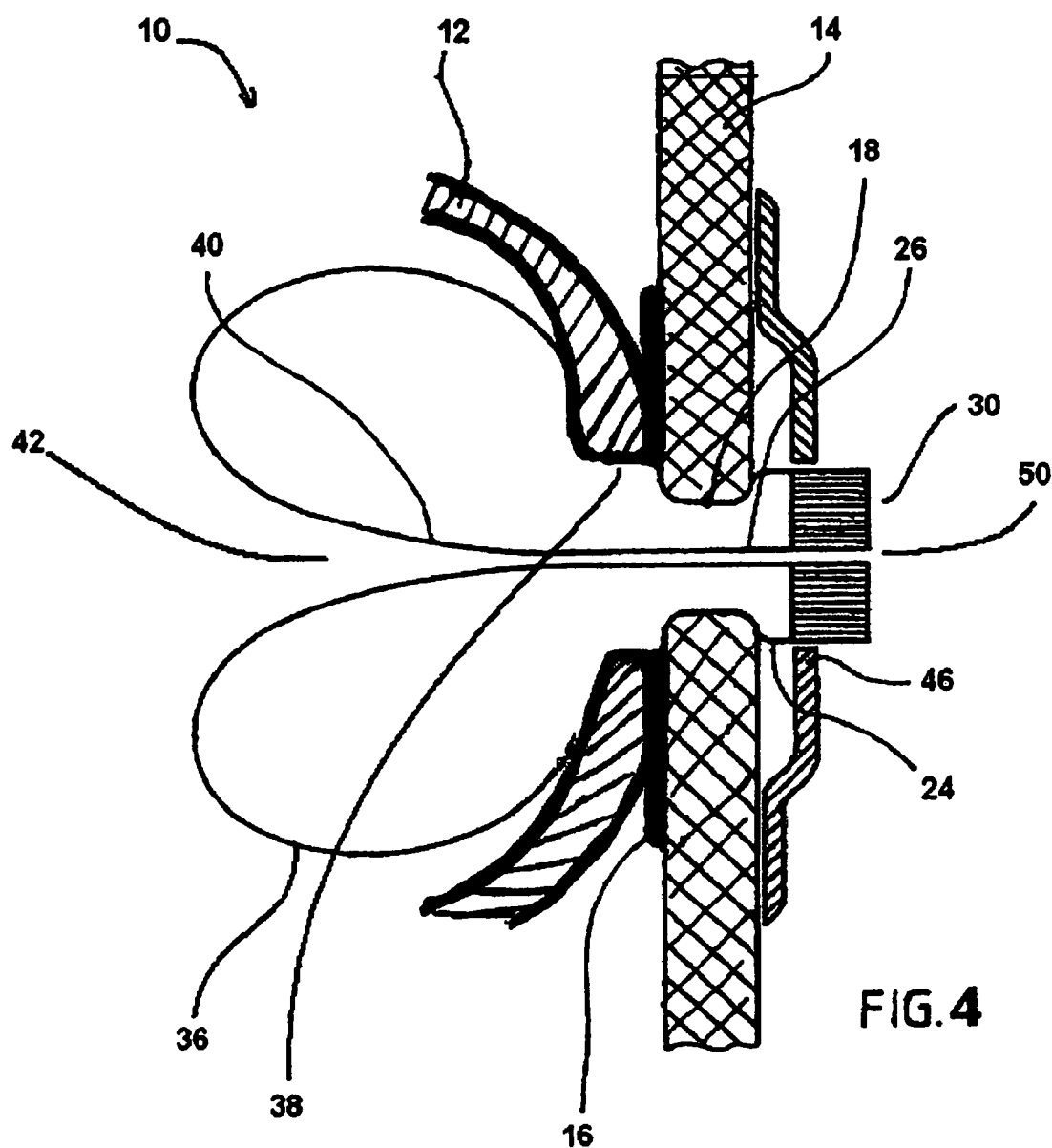
FIG. 4 depicts an alternative embodiment of the FIG. 1 device.

Turning now to FIG. 4, it may be seen that by giving the trans-abdominal section, i.e., that portion of the balloon 36 that is in contact with the stoma site 18, appropriate dimensions, the device 10 when inflated may be enabled to produce a certain radial force onto the trans-abdominal structures of the surgically perforated fistula channel or stoma 18. This force would serve to keep the penetration channel under permanent expansion and would therefore provide an efficient seal against gastric material leaving the stomach and entering the peritoneal cavity between the stomach and abdominal wall 14. Moreover this feature could also slow or stop bleeding at the site and foster a permanent and continuous dilation of the stoma itself.

Continuing to look at FIG. 4, it may be seen that the outer of the two concentric foil ends, in this case end 24 is dimensioned in such a way, that the exterior surface 38 exceeds the diameter of the stoma perforation. This may be seen by viewing that portion of the exterior surface 38 in contact with the gastric wall 12. In many embodiments, the surface 38 may be made to exceed the stoma diameter by a significant amount. A significant amount may be thought of in general terms as an amount that exceeds the widest section of the perforation by at least about 10%, but may range significantly higher including ranges from about 25 to about 50% greater than the stoma diameter, and in some embodiments may range up to about 75% greater than the stoma diameter.

Due to the material selection of the balloon, the mechanical properties of the material, and the balloon's wall thickness, the device 10 may be designed to function at inflation pressures that inhibit bleeding in the stoma 18 without subjecting the foil to a tensive or extensive force. That is, the rest of the sheath, introverted in the transmural passage area, forms a tight closure in this section of the device by virtue of the proposed material wall thickness, discussed in greater detail below. This serves to prevent the escape of gastric secretions in spite of longitudinal folding of the exterior surface 38. Hemostatic inflation of the device 10 precisely tailored to the particular blood flow situation can thus be achieved in the area of the stoma perforation. When thin-walled balloon membranes with a residual dimension are used, the transmural force which the balloon exerts on the puncture channel corresponds largely to the inflation pressure measurable in the case in question.

In order to promote this radial expansion effect, the wall thickness of the balloon 36 would likely be no greater than about 100 micrometers, especially in those regions where radial expansion is desirable, such as at the trans-abdominal section. Even so, in many embodiments, the balloon may be made of a soft membrane having a wall thickness of from about 30 to about 60 micrometers. While devices having wall thicknesses in this particular range are well-suited for use as initial placement devices, where higher seal forces are desired, a structurally identical device which is anticipated to remain in place for long-term treatment could be made of even thinner walled, less pressure resistant materials. In such devices, it is envisioned that the outer or exterior surface 38 especially at the trans-abdominal region would not even exceed about 50 micrometers, and may actually be thinner, in the range of from about 10 to about 30 micrometers.

A material capable of functioning in the prescribed manner and capable of functioning with these wall thicknesses may be manufactured of Pellethane 2363 from DOW Chemical, a thermoplastic polyurethane. However, other materials having similar mechanical characteristics should work equally as well. Suitable materials would be mechanically low-compliant and therefore stable in shape under elevated balloon filling pressures. They would exhibit little volume expansibility, and as such, as in the example stated above, a polyurethane is particularly well-suited in this application. Such materials, even under heavy traction, would not permit any considerable shape deformation of the torus balloon and thus would minimize the possibility that the balloon could inadvertently slip through the gastric wall. This capability is of some importance so as to ensure the continued reliability of the device under conditions associated with daily use.

Figure 5:
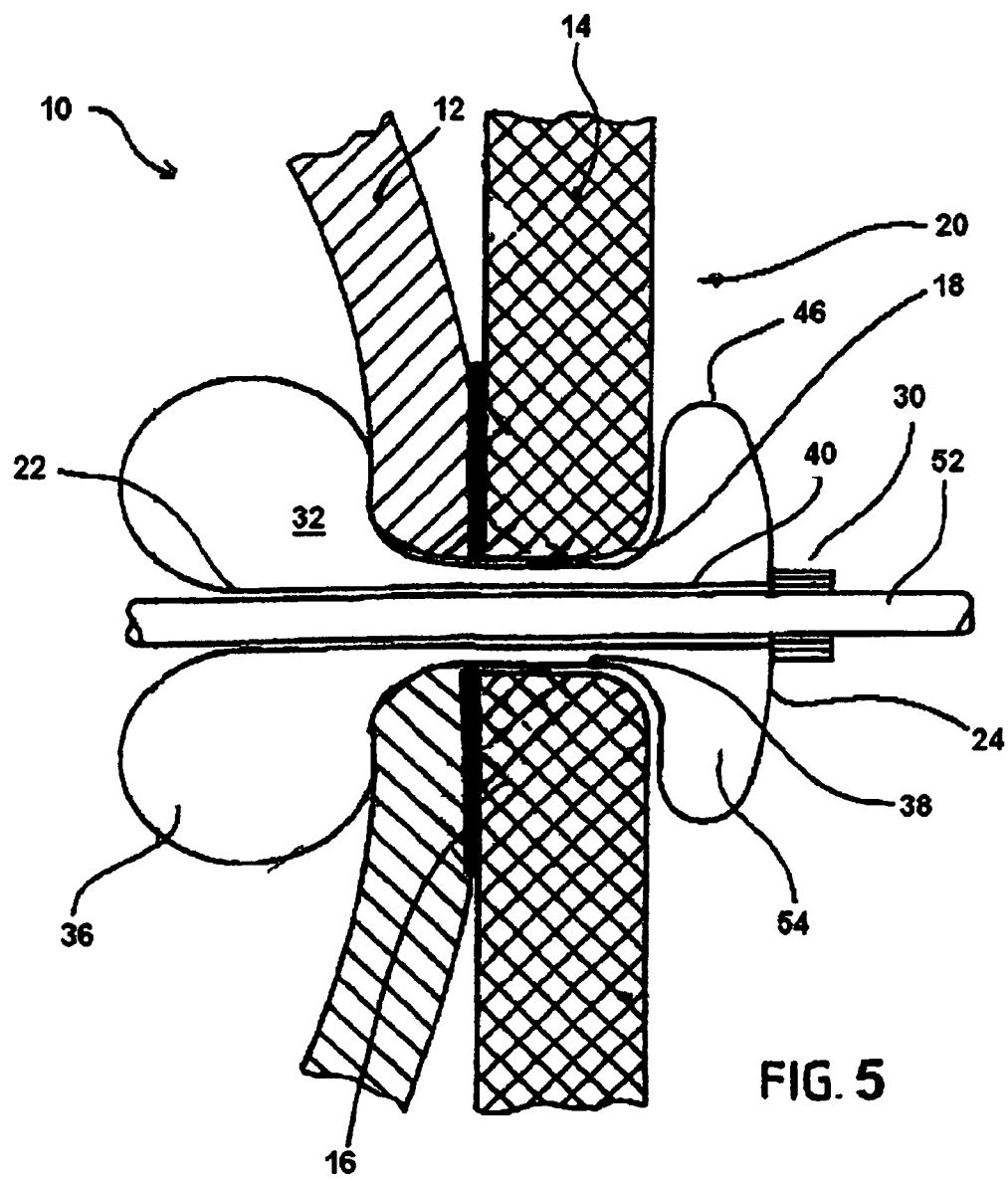
FIG. 5 depicts an alternative embodiment of the FIG. 1 device having a second embodiment of a useful retention mechanism.

FIG. 5 depicts an alternative embodiment of the device 10 having a bulge 54, in this case a disc-shaped bulge, formed into the exterior surface 38 of the balloon 36. This bulge 54, if present, would desirably be situated proximate to the end 24 such that it would be external to the stoma 18 and the living body 20 itself. The bulge 54 would serve as a second embodiment of the retention mechanism 46 and it may be seen that such a feature would counteract the force associated with the torus section of the balloon 36 internal to the living body 20. This embodiment may further facilitate homeostasis in the superficial wound area immediately after the perforation of the stoma 18. Moreover, the bulge 54 may also be desirable when a more rigid retention mechanism 46 can not be used due to the development of ulcers or other irritations of the skin.

In any of the aforementioned embodiments as well as in further embodiments described below, the foil 22 may be designed so that in the freely deployed state, that is, when the pressure within the space 32 is equal to the ambient environmental pressure, the exterior surface 38 of the balloon 36 at the trans-abdominal region may have a residual diameter which allows for the infolding of that surface 38 and thus provides for the best possible equalization of acting force and measured inflation pressure.

Figure 6:
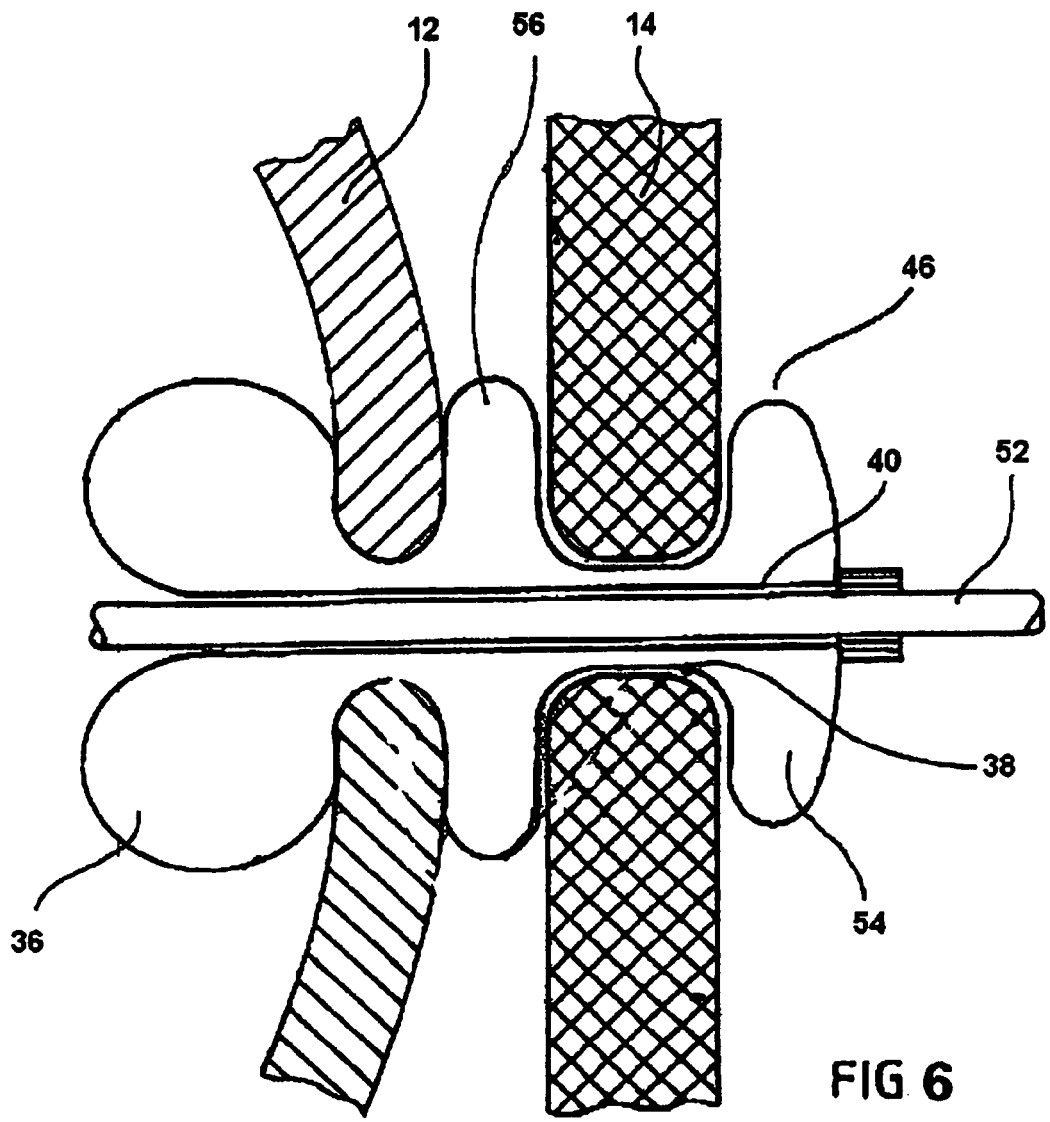
FIGS. 6 and 7 depict further embodiments of the device incorporating features from the FIG. 1 device as well as the second embodiment of retention mechanism.

Turning now to FIG. 6, it may be seen that a version of the device 10 may be manufactured so as to place a secondary bulge 56 between the gastric wall 12 and the abdominal wall 14. Such a device 10 would serve as a bolster against the intra-gastric balloon 36, and thus would enable a fluid tight seal and/or a haemostatic compression against gastric perforation when the balloon 36 and secondary bulge 56 were inflated. This may be of use, for example, in situations in which a patient has suffered a severe perforation and its associated bleeding. The device of FIG. 6 would enable the clinician to perform efficient compression of the puncture site. That portion of the device which would serve as the anchor or retention mechanism external to the living body 20 may consist of the bulge 54 or of a retention mechanism 46 similar to that shown in FIG. 1 or 4.

Figure 7:
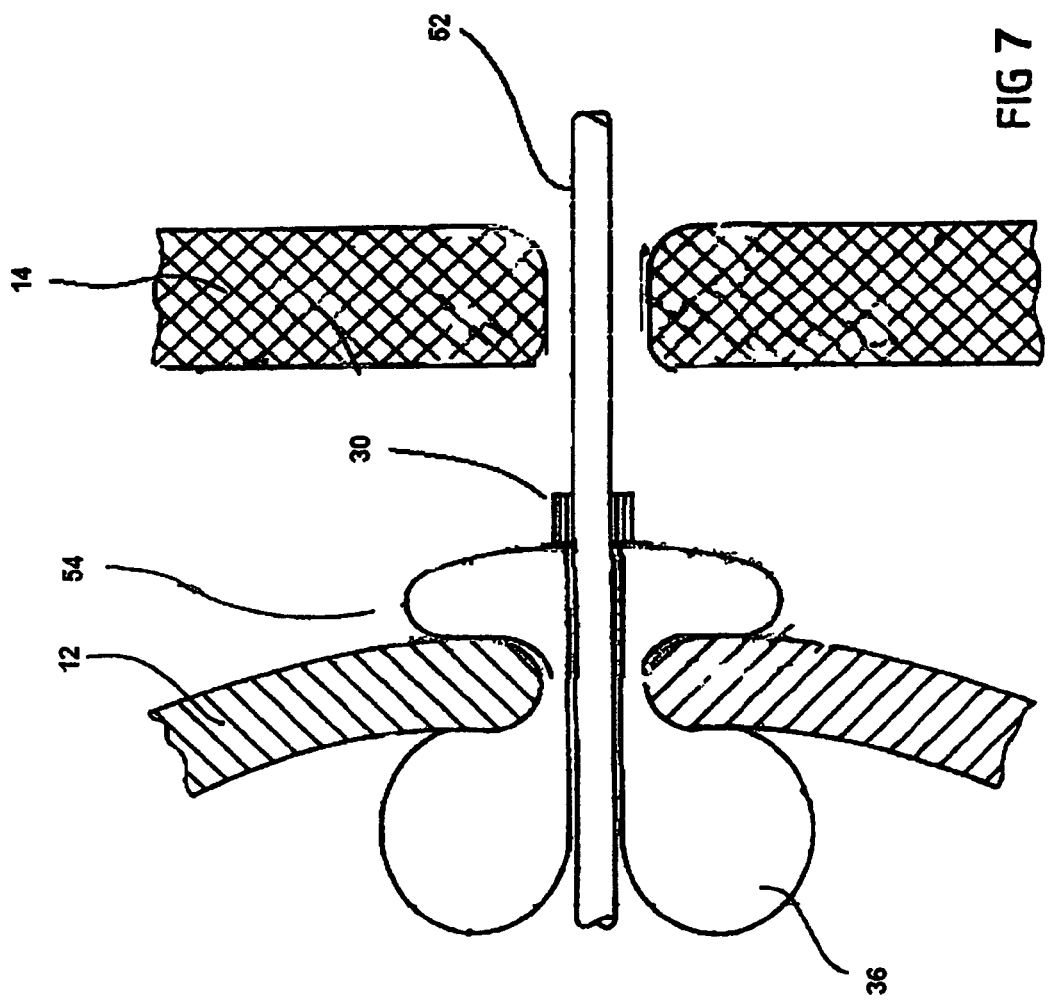

FIG. 7 shows yet a further alternative version of the device 10. The FIG. 7 embodiment depicts the torus shaped balloon 36 portion as being established inside the gastric wall 12 yet has no direct anchoring capability outside the abdominal wall 14. Such an intra-abdominal device grants free abdominal movement of the perforated organ and would also enable gastric access, yet the gastric wall 12 and the abdominal wall 14 would not be brought into direct contact and would thus not fuse to one another. This may be desirable for some medical or anatomical reasons. In this example, the device would be connected to the body outside through a hose connection.

As shown in FIGS. 5 through 7 the catheter may be used in any of the embodiments, including the others described herein. In particular, having the ability to slide a catheter 52 through the bore 50 and passage 42 into the stomach or other site internal to the living body 20 would be beneficial in cases of long-term use, as the catheter 52 could be changed simply and atraumatically, i.e. without damaging the puncture channel, and it could be accomplished even by a trained layperson.

Figure 8:
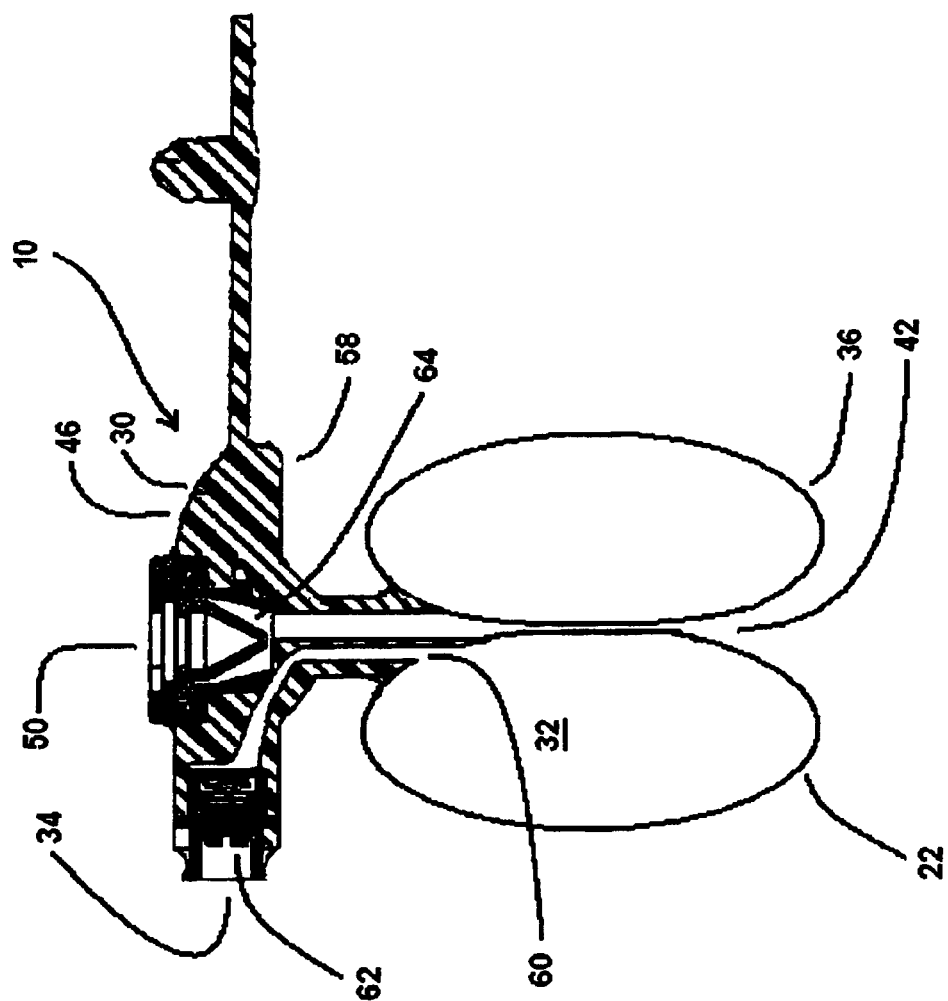
FIG. 8 depicts yet another embodiment of the device incorporating a third embodiment of the retention mechanism.

Referring to FIG. 8 there is shown a cross-sectional view of still another embodiment of the present invention. This embodiment is similar to the previous embodiments in that the balloon 36 may be configured similarly to any of the balloon embodiments described above. Like the prior embodiments, the FIG. 8 embodiment includes the thin foil 22 having a length 28 terminating in the first and second ends 24 and 26. Additionally, one end is backfolded or introverted with respect to the other so as to create the space 32 that forms the balloon 36 between the two ends 24 and 26 respectively. However, FIG. 8 depicts yet a third embodiment of the retention mechanism 46. In that FIG. 8 forms a more detailed cross-sectional view of one possible embodiment, a number of items are described as pertaining to FIG. 8. It should be noted that these items may also be found on other embodiments, including those described above. Those items not capable of being utilized on previous embodiments will be specifically noted.

In more general terms, this embodiment integrates the retention mechanism 46 into the cap 30 itself. As such, the two components may be thought of as forming a head 58. The head 58 serves at least in part to capture the ends 24 and 26 but also serves to contain a valve or valves which are used to regulate the flow of fluids through the entire device 10. As such, the head 58 may be made of a medical grade silicone but should be sufficiently designed to capture the foil ends 24 and 26 without undue failure. As is the case with each embodiment of the retention mechanism 46, the head 58 also serves to prevent the device 10 from completely advancing through the stoma 18 and into the stomach or intestine of the living body 20.

A first of said valves would serve as the port 34 and as such would be adapted to couple the space 32 with the inflation source or mechanism 44. As in the previous embodiments, the port 34 would serve as a means to inject fluids into or remove fluids from the space 32 forming the interior of the balloon 36. A lumen 60 may be provided that leads from the port 34 to the space 32. Such a lumen 60 though not shown may be desirable on each of the other embodiments. As would be apparent, control of the inflation mechanism 44 through the port 34 enables the user or a physician, etc., to selectively control inflation and deflation of the balloon 36. To assist in this, a releasable one-way valve 62 may be disposed between the space 32 and the port 34, for example in the lumen 60. Appropriate valves capable of serving in this function are known and would be understood by those having skill in the art and may be actuated by means of a syringe.

A second of said valves, if provided, may be situated in the bore 50 located in the head 58 and would enable the injection of enteral feeding solution, etc., through the device 10 and into the user. The valve may comprise an anti-reflux valve 64 which is configured to allow nutrient solutions, etc., to pass into the user, but to prevent the flow of fluids out of the user unless properly engaged by a syringe or other sampling device having a nipple which corresponds to the anti-reflux valve. The anti-reflux valve 64 would be disposed such that it is in communication with the passage 42.

Figure 9:
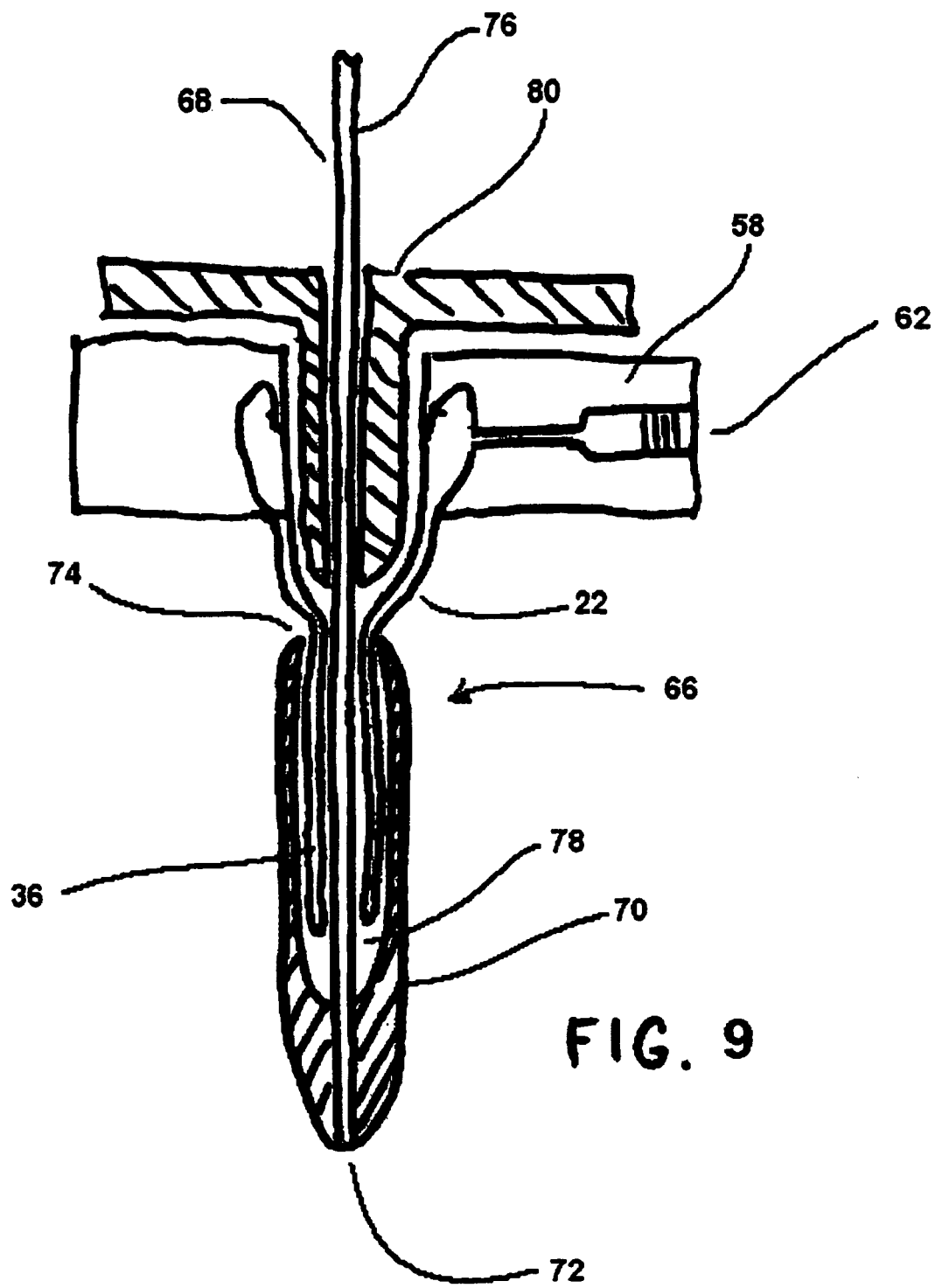
FIG. 9 depicts an insertion device adapted to be used with the FIG. 8 embodiment.

Looking now to FIG. 9, the FIG. 8 embodiment is depicted in conjunction with an insertion device 66. The insertion device 66 may be configured as a user manipulable introducer 68 having a hollow probe 70 at one end. The probe 70 may be tapered at a distal end 72 to allow ease of passage through the stoma 18 so as to minimize aggravation of the tissue. A proximal end 74 of the probe 70 may also be tapered to allow subsequent withdrawal of the probe 70 from the stoma 18 with minimal tissue damage as well. Protruding from the proximal end 74 is an extension rod 76 adapted to be grasped by the user, physician, or clinician. The rod 76 may be configured as a hollow cannula so as to be deployable over a guide wire (not shown) previously placed within the living body 20.

Prior to installation in the living body 20, the foil 22 is captured within a cavity 78 formed in the hollow probe 70. The extension rod 76 is situated so as to extend from the cavity 78, through the passage 42 and the bore 50, and ultimately extend outward through the head 58. A capturing element 80 is designed to be slid over the extension rod 76 and seated within the bore 50 in the head 58. By ensuring that the capturing element 80 is held in contact with the foil 22, which in turn is pressed against proximal end 74 of the probe 70, the insertion device 66 may be placed in situ within the cavity.

Once the foil 22 is in place, the user would continue to advance the probe 70 deeper into the living body 20 until the foil 22 is adequately deployed from the cavity 78. Prior to or during this step, the capturing element 80 may be removed from the extension rod 76 or at least backed away from the probe 70. This may all be accomplished by manipulation of the extension rod 76. Subsequent inflation of the balloon 36 would ensure that the foil 22 is completely free of the cavity 78. After the balloon 36 is inflated, the probe 70 may be withdrawn from the living body by backing it out through the passage 42 and the bore 50, and ultimately completely removing it from the device 10.

Figure 10:
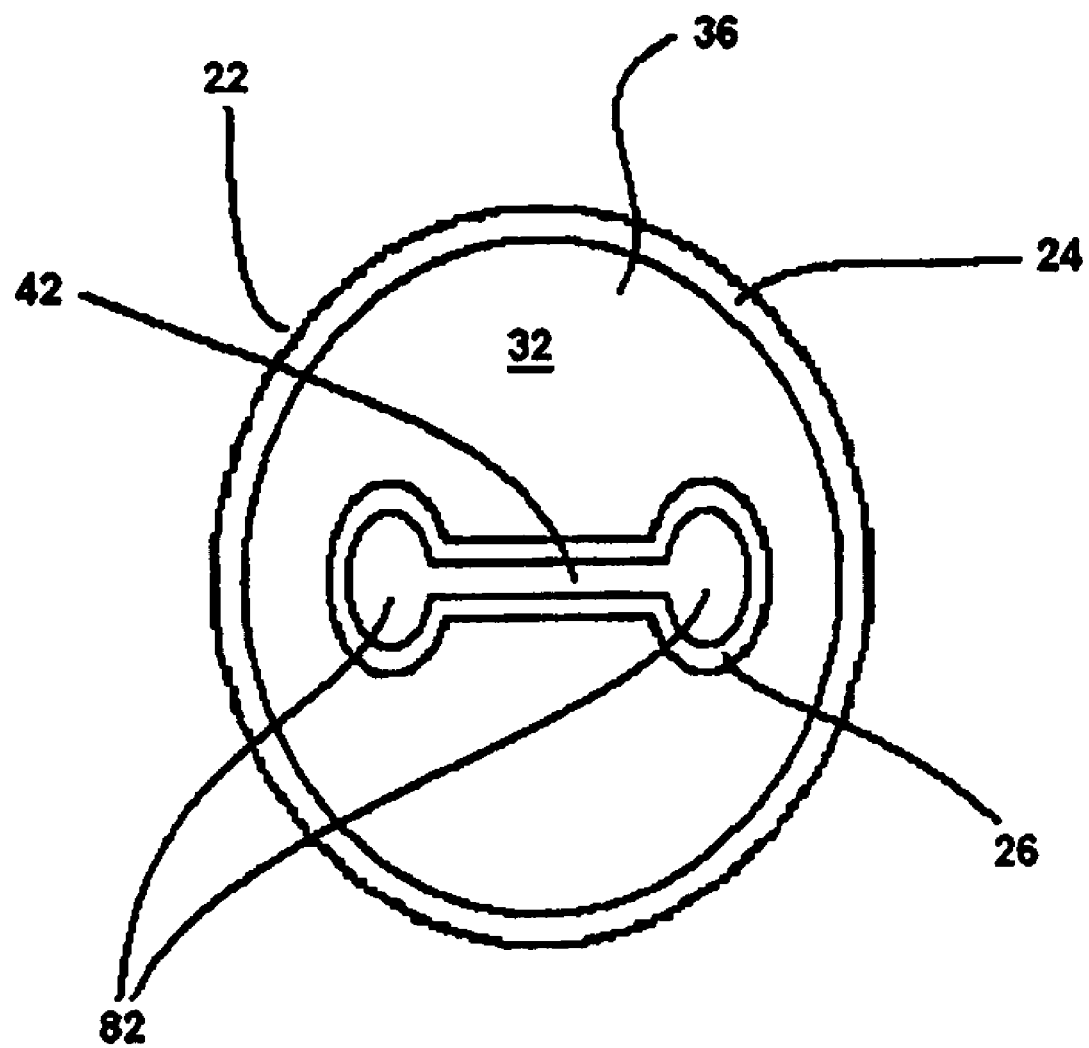
FIG. 10 depicts a channel enabling venting of the device; such a channel may be used on any embodiment of the device described herein.

Finally, FIG. 10 has been included to address ventilation of the living body 20. In FIG. 10, it may be seen that the channel 42 contained within the balloon 36 may be shaped in order to prevent its total collapse into the tape-like structure. That is, by manufacturing the end 26 as well as a portion of the interior surface 40 to a given foil wall thickness, one can prevent a total collapse of the channel 42, and instead it is possible to form one or more laterally positioned tubular paths 82. These tubular paths 82 would serve to grant a permanent, noncollapsible passageway for gases. The diameter of the resulting tubular paths 82 may be configured by choosing an appropriate wall thickness of the foil 22. Alternatively a tubular reinforcement exhibiting an appropriate stiffness may be inserted and permanently affixed within the channel 42. This may be desirable in instances as described above where a patient having an existing anatomical or functionally insufficient communication between the stomach and the ambient surrounding of the patient requires the release of accumulating stomach gases As used herein and in the claims, the term "comprising" is inclusive or open-ended and does not exclude additional unrecited elements, compositional components, or method steps.

While various patents have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

We claim:

1. A device (10) for the creation of an artificial stoma (18) into and subsequent fluid transfer to or from a living body (20) comprising:
   a thin foil (22) having a first and a second end (24, 26) with a length (28) disposed therebetween, the thin foil (22)

being arranged in a manner such that one of said ends is backfolded or introverted into the other of said ends; and a cap (30) having at least one port (34) therethrough, the cap (30) securely capturing each end (24, 26) of the foil (22) therein, the port terminating between the first and second foil ends (24, 26) within a space (32) created by introversion of the foil (22) so that application of an inflation source (44) to the port (34) causes the length (28) of said foil (22) to inflate and form a generally torus shaped balloon (36) having exterior and interior externally facing concentric surfaces (38, 40); and an insertion device (66) comprising a user manipulable introducer (68) and a capturing element (80) for placing the foil (22) in a deflated state within the living body (20) and situating the cap (30) adjacent a body surface at the stoma (18), wherein the introducer (68) comprises a tapered probe (70) having a cavity (78) therein within which the foil (22) is temporarily captured, and the capturing element (80) is sized to fit frictionally within a bore (50) in the cap and in conjunction with the foil (22) retain the introducer (68) in position proximate to the cap (30).

2. The device (10) of claim 1 wherein the bore (50) is in communication with a passage (42) formed by the interior externally facing surface (40) which passes through the interior of the device (10).

3. The device (10) of claim 1 wherein the torus shaped balloon (36) is adapted to exert an increasingly greater force upon increasing inflation, the force being exerted axially along the foil (22) and directed toward the cap (30).

4. The device (10) of claim 1 comprising an extension rod (76) affixed to the introducer (68), the extension rod (76) enabling the tapered probe (70) to be inserted deeper into the living body (20) until the foil (22) is disengaged from within the cavity (78) without affecting the position of the cap (30) or the capturing element (80).

5. The device (10) of claim 4 wherein the introducer (68) is removed from the living body (20) via the passage (42) and bore (50) subsequent to the inflation of the balloon (36) and removal of the capturing element (80).

6. The device (10) of claim 1 adapted to be placed in the living body (20) by engaging a guide wire previously situated in the living body (20).

7. The device of claim 1 further comprising, when inflated, a bulge (54) formed into the exterior surface (38) upon inflation of the balloon (36), the bulge (54) being proximate the end (24) of the foil (22) and adjacent the cap (30) securing each end (24,26) of the foil (22).

* * * * *